(12) United States Patent
Butler (10) Patent No.: US 7,001,413 B2
(45) Date of Patent: Feb. 21, 2006

(54) METHODS AND APPARATUS FOR LIGHT THERAPY

(75) Inventor: Glenn Butler, Tarrytown, NY (US)

(73) Assignee: Life Support Technologies, Inc., Tarrytown, NY (US)

( * ) Notice: Subject to any disclaimer, the term of this patent is extended or adjusted under 35 U.S.C. 154(b) by 0 days.

(21) Appl. No.: 10/613,608

(22) Filed: Jul. 3, 2003

(65) Prior Publication Data

US 2004/0008523 A1    Jan. 15, 2004

Related U.S. Application Data

(60) Provisional application No. 60/393,607, filed on Jul. 3, 2002, provisional application No. 60/430,269, filed on Dec. 2, 2002.

(51) Int. Cl.
*A61N 5/01* (2006.01)
(52) U.S. Cl. .................. 607/88; 128/898; 607/100
(58) Field of Classification Search .............. 606/9, 606/4–5; 607/88–94
See application file for complete search history.

(56) References Cited

U.S. PATENT DOCUMENTS

| | | | | |
|---|---|---|---|---|
| 4,930,504 A | * | 6/1990 | Diamantopoulos et al. | ... 607/88 |
| 5,151,096 A | | 9/1992 | Khoury | |
| 5,278,432 A | | 1/1994 | Ignatius et al. | |
| 5,413,587 A | | 5/1995 | Hochstein | |
| 5,562,656 A | * | 10/1996 | Sumiya | ...... 606/4 |
| 5,645,550 A | * | 7/1997 | Hohla | ...... 606/108 |
| 5,649,972 A | | 7/1997 | Hochstein | |
| 5,660,461 A | | 8/1997 | Ignatius et al. | |
| 5,698,866 A | | 12/1997 | Doiron et al. | |
| 5,728,090 A | | 3/1998 | Martin et al. | |
| 5,860,967 A | * | 1/1999 | Zavislan et al. | ...... 606/9 |
| 5,938,657 A | * | 8/1999 | Assa et al. | ...... 606/9 |
| 6,019,482 A | | 2/2000 | Everett | |
| 6,048,359 A | | 4/2000 | Biel | |
| 6,221,095 B1 | | 4/2001 | Van Zuylen et al. | |
| 6,241,697 B1 | | 6/2001 | Augustine | |
| 6,290,713 B1 | | 9/2001 | Russell | |
| 6,334,069 B1 | | 12/2001 | George et al. | |
| 6,353,763 B1 | | 3/2002 | George et al. | |
| 6,618,620 B1 | * | 9/2003 | Freundlich et al. | ...... 607/27 |
| 6,641,578 B1 | * | 11/2003 | Mukai | ...... 606/9 |
| 2002/0026180 A1 | * | 2/2002 | Nakamura | ...... 606/5 |
| 2002/0120312 A1 | * | 8/2002 | Ignatius et al. | ...... 607/90 |
| 2003/0004499 A1 | * | 1/2003 | McDaniel | ...... 606/3 |
| 2004/0098069 A1 | * | 5/2004 | Clement et al. | ...... 607/88 |
| 2004/0158300 A1 | * | 8/2004 | Gardiner | ...... 607/88 |
| 2004/0215176 A1 | * | 10/2004 | Bahk | ...... 606/11 |

FOREIGN PATENT DOCUMENTS

DE    3837248 A1 *   5/1990

* cited by examiner

*Primary Examiner*—Henry M Johnson, III
(74) *Attorney, Agent, or Firm*—Dugan & Dugan (57) ABSTRACT

In a first aspect, an apparatus for use in light therapy is provided that includes (1) at least one light emitting diode array adapted to emit a wavelength of light; and (2) a targeting mechanism coupled to the at least one light emitting diode array so as to allow light emitted from the at least one light emitting diode array to be repeatably positioned on a target area during non-contact light therapy. Numerous other aspects are provided.

10 Claims, 10 Drawing Sheets

METHODS AND APPARATUS FOR LIGHT THERAPY

The present application claims priority from U.S. Provisional Patent Application Ser. No. 60/393,607, filed Jul. 3, 2002 and U.S. Provisional Patent Application Ser. No. 60/430,269, filed Dec. 2, 2002, both of which are hereby incorporated by reference herein in their entirety.

FIELD OF THE INVENTION

The present invention relates generally to the use of electromagnetic energy during medical treatment, and more particularly to methods and apparatus for light therapy.

BACKGROUND OF THE INVENTION

Visible and near infrared wavelength light is known to have many therapeutic benefits. For example, wavelengths of 680, 730 and/or 880 nanometers have been shown to increase cell growth and speed wound healing (especially when combined with hyperbaric oxygen), and have been used to activate photoactive agents for various cancer treatments. Whelan et al., "NASA Light Emitting Diode Medical Applications From Deep Space to Deep Sea," Space Technology and Applications International Forum—2001, American Institute of Physics, pp. 35–45 (2001).

Despite the recognition of the benefits of visible and near infrared wavelength light irradiation, there remains a need for methods and apparatus for carrying out these and other forms of light therapy.

SUMMARY OF THE INVENTION

In a first aspect of the invention, an apparatus for use in light therapy is provided that includes (1) at least one light emitting diode array adapted to emit a wavelength of light; and (2) a targeting mechanism coupled to the at least one light emitting diode array so as to allow light emitted from the at least one light emitting diode array to be repeatably positioned on a target area during non-contact light therapy.

In a second aspect of the invention, an apparatus for use in light therapy is provided that includes (1) at least one light emitting diode array adapted to emit a wavelength of light; (2) a targeting mechanism that includes at least one targeting light source coupled to the at least one light emitting diode array so as to allow light emitted from the at least one light emitting diode array to be repeatably positioned on a target area, wherein the targeting light source is adapted to turn off prior to image recording; and (3) an imaging mechanism adapted to image the target area.

Numerous other aspects are provided, as are methods and computer program products for carrying out these and other aspects of the invention. Each computer program product described herein may be carried by a medium readable by a computer (e.g., a carrier wave signal, a floppy disc, a compact disc, a DVD, a hard drive, a random access memory, etc.).

Other features and aspects of the present invention will become more fully apparent from the following detailed description, the appended claims and the accompanying drawings.

DETAILED DESCRIPTION

Figure 1:
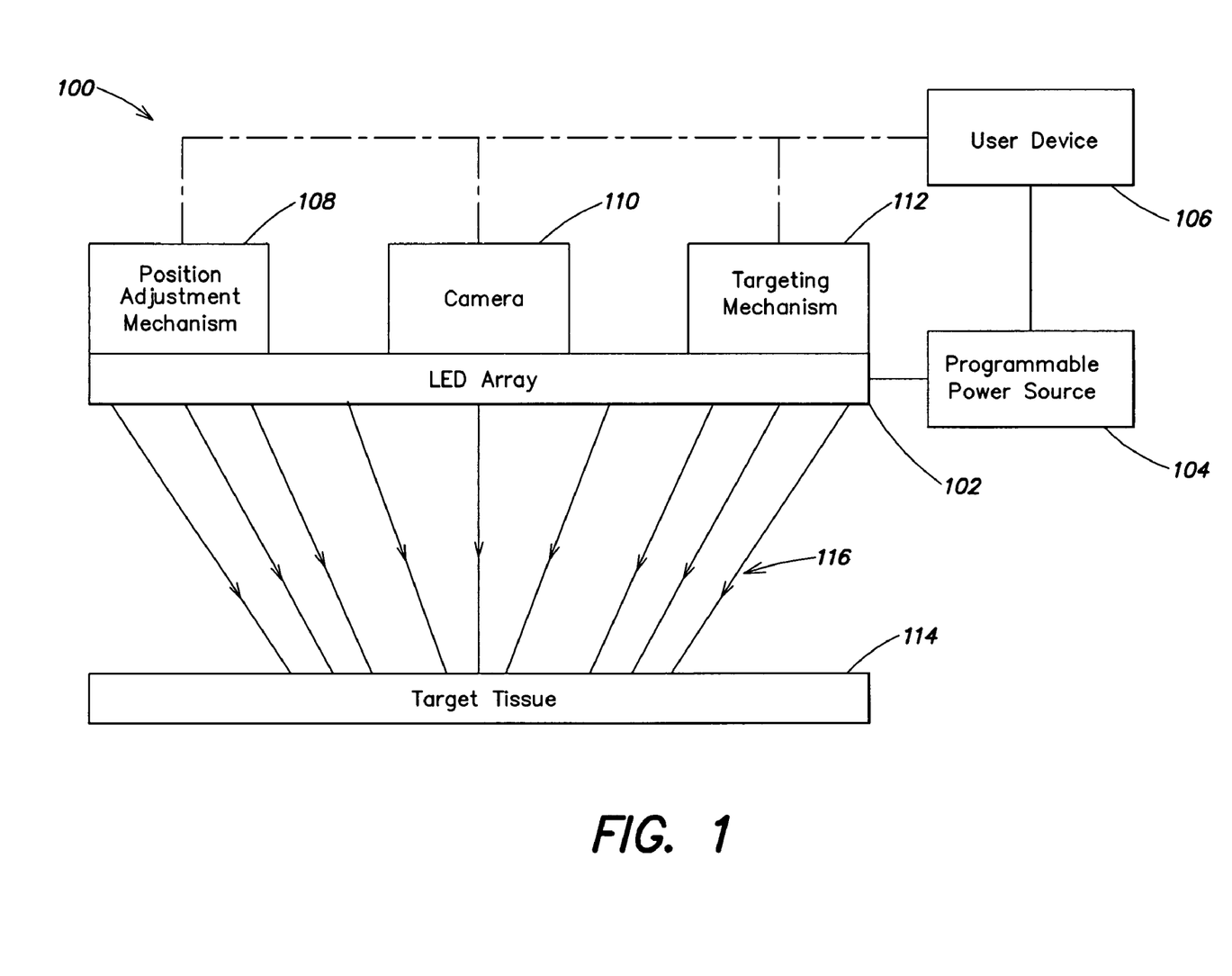
FIG. 1 is a block diagram of a first embodiment of a light therapy device provided in accordance with the present invention.

FIG. 1 is a block diagram of a first embodiment of a light therapy device 100 provided in accordance with the present invention. With reference to FIG. 1, the light therapy device 100 includes a light emitting diode (LED) array 102 in communication with a programmable power source 104, and a user device 106 in communication with the programmable power source 104. The light therapy device 100 also may include one or more of a position adjustment device 108, a camera 110 and a targeting mechanism 112. As will be described further below, the light therapy device 100 allows for non-invasive, repeatable dose light therapy of a target area (e.g., target tissue 114 in FIG. 1) using one or more wavelengths of light. Such light therapy may employed, for example, to stimulate new growth in chronic wounds, to kill pathogenic organisms, to activate photo sensitive chemicals for treatment of skin or other cancers, or for any similar purpose.

With reference to FIG. 1, the LED array 102 comprises a plurality of LEDs (not separately shown in FIG. 1) each adapted to emit light within a predetermined wavelength range (e.g., about a specific center frequency or wavelength). The LEDs of the LED array 102 may be adapted to emit the same wavelength, or one or more different wavelengths. In at least one embodiment of the invention described below with reference to FIGS. 3A–B, the LED array 102 comprises a plurality of sub-arrays each adapted to emit a different wavelength. For example, one sub-array of LEDs may be adapted to emit near-infrared light (e.g., light having a wavelength within the range from about 1000 to 800 nanometers), one sub-array of LEDs may be adapted to emit visible light (e.g., light having a wavelength within the range from about 800 to 400 nanometers), and another sub-array of LEDs may be adapted to emit ultraviolet light (e.g., light having a wavelength within the range from about 400 to 200 nanometers). Other combinations and numbers of wavelengths of light may be employed, as may other wavelength ranges. The LEDs employed within the LED array 102 may comprise any conventional light emitting diodes adapted to emit light of the desired wavelength/frequency.

The programmable power source 104 may comprise any conventional power source capable of driving the LEDs of the LED array 102 (e.g., any power source capable of providing one or more driving voltages and/or currents with a desired amplitude, frequency, duration and/or duty cycle to the LEDs). In one embodiment of the invention, the programmable power source 104 comprises a model No. MS210 four-channel mixer and a model no. PS24 twenty-four volt power supply available from Advanced Illumination of Rochester, Vt., although any other programmable power source may be similarly employed. A non-programmable power source also may be employed.

The user device 106 may comprise, for example, a desktop computer, a laptop computer, a microcontroller, a personal digital assistant (PDA), a keyboard or other interface to the programmable power source 104 or the like. In at least one embodiment of the invention, the user device 106 is adapted to interface with and control the programmable power source 104 (e.g., by allowing a user to specify the amplitude, frequency, duty cycle and/or duration of one or more power signals applied to the LED array 102 by the power source 104). The user device 106 also may be employed to control one or more of the position adjustment mechanism 108, the camera 110 and/or the targeting mechanism 112.

The position adjustment mechanism 108 may comprise any mechanism capable of repeatably positioning the LED array 102 relative to a target such as the target tissue 114. In the embodiment of the light therapy device 100 described below with reference to FIGS. 3A–B, the position adjustment mechanism 108 comprises an articulated arm. Any other conventional positioning device may be similarly employed for the position adjustment mechanism 108, such as an x-y-z stage (with or without motorized control), a slideable rail system, etc.

The camera 110 may comprise any conventional imaging system for viewing a target area such as the target tissue 114. For example, the camera 110 may comprise a digital or analog (film) camera, a charge-coupled device, a digital or analog video system or the like. In at least one embodiment of the invention, the camera 110 comprises a digital camera capable of capturing images of a target area for storage and/or manipulation by the user device 106 (e.g., in a TIF, JPEG or other known format).

Figure 3A:
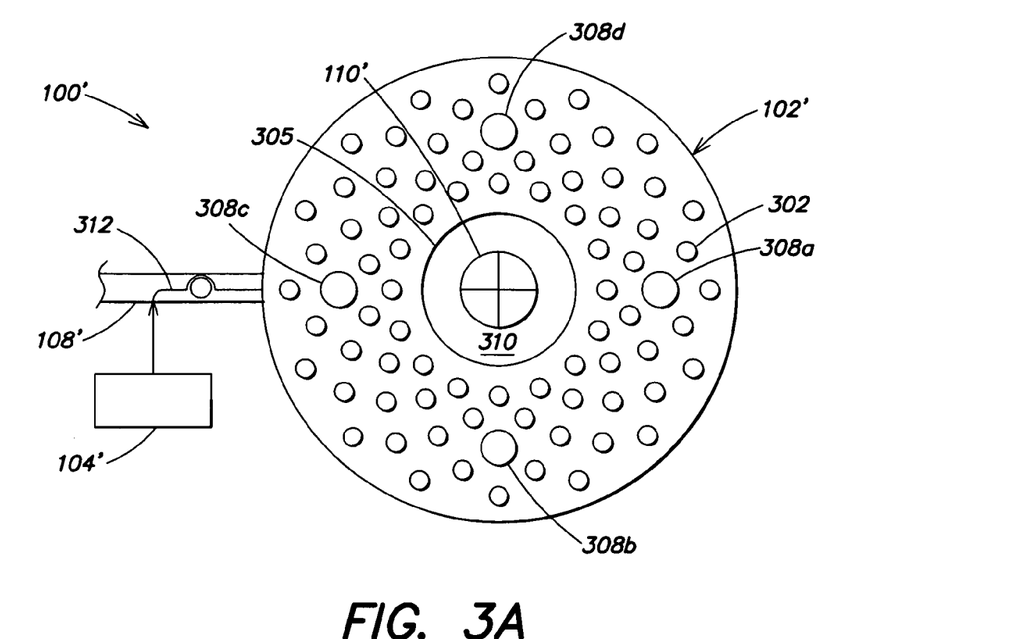
FIGS. 3A–B are a schematic bottom view and side view, respectively, of an exemplary embodiment of the light therapy device of FIG. 1.
Figure 3B:
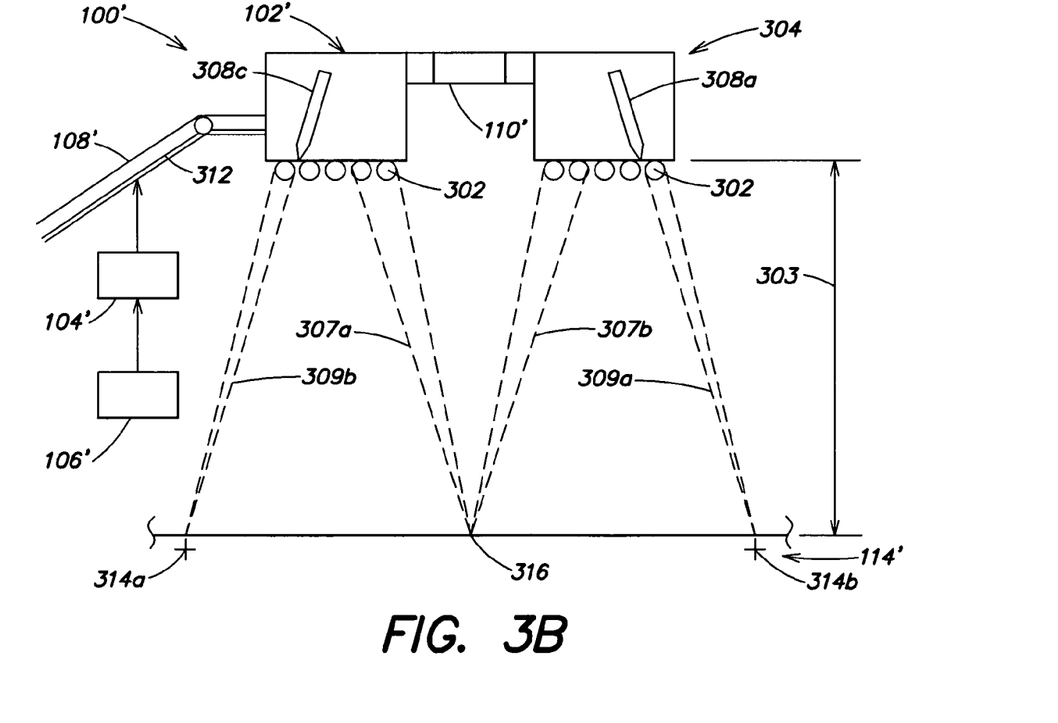

The targeting mechanism 112 may comprise any mechanism that allows light beams emitted from the LED array 102 to be repeatably positioned on a target area such as the target tissue 114. In the embodiment of FIGS. 3A–B, the targeting mechanism 112 comprises one or more lasers for generating one or more light beams on a target area (e.g., one or more visible light beams). The one or more light beams may be used, for example, to identify the outermost area irradiated by the LED array 102. Other suitable targeting mechanisms may include, for example, crosshairs, viewfinders, etc.

The position adjustment mechanism 108, the camera 110 and/or the targeting mechanism 112 may operate independently, or in cooperation, so as to form an overall target positioning system that may or may not be in communication with the user device 106. Those skilled in the art will understand that devices in communication with each other need only be "capable of" communicating with each other and need not be continually transmitting data to or receiving data from each other. On the contrary, such devices need only transmit data to or receive data from each other as necessary, and may actually refrain from exchanging data most the time. Further, devices may be in communication even though steps may be required to establish a communication link. Such communication may be performed over any suitable channel or combination of channels including for example, wireless, hardwired, optical or other channel types.

Although not shown in FIG. 1, the light therapy device 100 may include one or more focusing devices for focusing light emitted from the LED array (identified by reference numeral 116 in FIG. 1) onto a target area. Such focusing devices are well known, and may include, for example, one or more appropriately selected optical components such as a lens.

Figure 2:
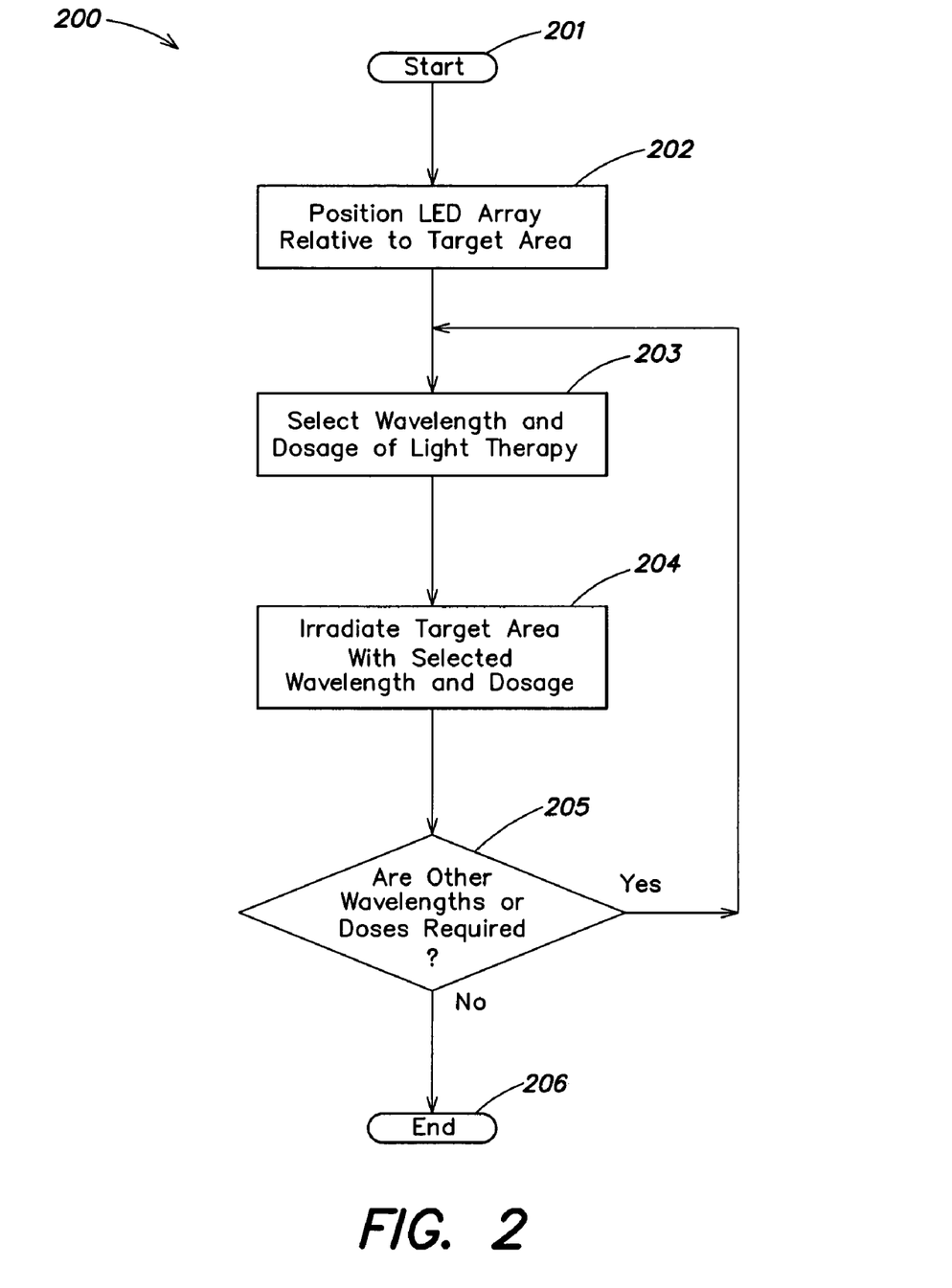
FIG. 2 is a flowchart of an exemplary process that may be performed by the light therapy device of FIG. 1.

FIG. 2 is a flowchart of an exemplary process 200 that may be performed by the light therapy device 100 of FIG. 1. One or more of the steps of the process 200 may be implemented as one or more computer program products stored, for example, in the user device 106.

With reference to FIG. 2, the process 200 begins with step 201. In step 202, the LED array 102 is positioned relative to the target area (e.g., target tissue 114). Positioning of the LED array 102 may be achieved by employing one or more of the position adjustment mechanism 108, the camera 110 and the targeting mechanism 112 (as described further below). Following positioning of the LED array 102, the camera 110 may be employed to image the target area. In an embodiment wherein the targeting mechanisms 112 includes one or more targeting lasers for positioning and/or ranging (as described below with reference to FIGS. 3A and 3B), laser beam features such as intersection points, crosshairs or the like may be imaged with the target area (e.g., to aid in repeatable positioning of the LED array 102 relative to the target area at a later time).

In step 203, a wavelength and dosage of light therapy is selected. This may be performed, for example, via the user device 106 and/or the programmable power source 104. Assuming the LED array 102 is capable of producing multiple wavelengths via a plurality of LED sub-arrays (e.g., each sub-array generating a different wavelength), the programmable power source 104 may be configured to independently drive each subarray of LEDs. In the embodiment of the invention described below with reference to FIGS. 3A–B, this is achieved by associating each sub-array of LEDs with a different, programmable channel of the programmable power source 104.

Employing either the user device 106 or the programmable power source 104, a user may select a wavelength of light with which to irradiate a target area, and the dose of the light to deliver. Dose may be set via selection of amplitude, duty cycle and/or duration of the power signal or signals used to drive the LEDs which generate the selected wavelength of light. In at least one embodiment, the user device 106 may be provided with dose recipes which represent predetermined power signal amplitudes, duty cycles and/or durations for one or more light doses. Accordingly, a user need only select a desired dose without having to determine power signal amplitude, duty cycle, duration or the like.

Once a wavelength and dosage of light therapy has been selected, in step 204 the target area is irradiated with the selected wavelength and dosage (e.g., via application of the appropriate power signal or signals to the LED array 102 via the programmable power source 104).

In step 205, it is determined whether any other wavelengths or doses of light therapy are to be applied to the target area. If so, the process 200 returns to step 203 for selection of the next wavelength and/or dosage of light therapy; otherwise the process 200 ends in step 206. Note, the process 200 may include a step of documenting the performed light therapy such as taking one or more images of the target area, recording dose or exposure information, etc., with the user device 106.

It will be understood that multiple wavelengths may be applied (e.g., simultaneously) during step 204, and that wavelength selection may occur prior to positioning of the LED array 102.

FIGS. 3A and 3B are a schematic bottom view and side view, respectively, of an exemplary embodiment of the light therapy device 100 of FIG. 1 (referred to by reference numeral 100' in FIGS. 3A–B). As will be described further below, the light therapy device 100' of FIGS. 3A–B may provide clinically repeatable dosages of near infrared (NIR), ultra-violet (UV) and other light frequencies to stimulate new growth in chronic wounds, to kill pathogenic organisms, to activate photo sensitive chemicals in the treatment of skin and other cancers, etc.

In the embodiment of FIGS. 3A and 3B, the light therapy device 100' employs four different LED wavelengths within the range from about 200 to 1000 nanometers. It will be understood that in general, any number of independently controlled LED wavelengths may be employed (e.g., for specific clinical applications), and that other wavelengths may be employed.

With reference to FIG. 3A, the light therapy device 100' includes an LED array 102' having one-hundred twenty LEDs 302 (not all one-hundred twenty of which are illustrated in FIG. 3A) configured in a circular arrangement. The LED array 102' is divided into four sub-arrays (not separately shown) of LEDs which emit four different wavelengths (frequencies). In at least one embodiment, the four wavelengths emitted by the four LED sub-arrays are 350, 590, 660, and 880 nanometers, although other wavelengths may be employed. The shorter wavelengths may be desirable as 590 nm may provide the shorter wavelength needed to resonate low molecular weight growth factors, and 350 nm is a photochemical frequency responsible for the production of Vitamin D3 and melanin in human skin and is known to be moderately pathogenic to most infecting organisms.

Each of the four LED sub-arrays represents an isolated circuit of 30 LEDs, 29 of which are arranged in a 360-degree pattern of light distribution that is equal as compared to the other LED sub-array patterns for uniform light distribution to a circular, rectangular or otherwise shaped target area (e.g., a tissue target area 114' in FIG. 3B). That is, LED's of differing frequencies are uniformly interdispersed (rather than having all LED's of the same frequency being grouped together). The remaining (one) LED of each sub-array is disposed on a backside of the LED array 102' and may be employed as an indicator light to identify when power is being applied to each LED sub-array. Such an LED array may be similar to a model no. CL 141A-4 Color RL36120 5" Ring Light available from Advanced Illumination but customized for the particular wavelengths being employed. Other LED arrays may be employed.

In at least one embodiment, the LED array 102' is arranged in a near flat circular plane that is directed and/or focused to a 150 mm per side square target when the LED array 102' is positioned at a distance 303 of 300 mm from a target area (e.g., tissue target area 114'). In such an embodiment, the outside diameter of the LED array 102' may be about 128 mm in diameter with an interior circular opening 305 of about 50 mm. Other LED array shapes, sizes, focal lengths and focal widths may be employed.

A four channel programmable power source 104' (e.g., a four channel programmable controller, a programmable voltage source, a microcontroller, or the like) is provided that can vary both the power signal applied to each 30 unit LED circuit/sub-array. For example, the programmable power source 104' may vary one or more of the voltage, current, amplitude, duty cycle, duration, etc., applied to each LED circuit/subarray. This feature permits controlled tissue "dosing" with each individual LED wavelength, or a specific pattern of wavelength exposure in order to provide the optimal exposure to promote growth, fight infection, or activate photodynamic compounds. In at least one embodiment, the power source 104' may be programmed via a user device such as a laptop or other computer 106'

As shown in both FIGS. 3A and 3B, the light therapy device 100' is equipped with a target positioning system 304 that includes lasers 308a–d, a camera 110' (e.g., a digital camera) and a computer based programmable controller and text/photo documentation system (e.g., one or more software programs operable with the laptop or other computer 106'). For example, the computer 106' may record and/or store patient medical information, wound measurements, wound photographs (e.g., provided via the camera 110') and repeatable dosage exposures of the wound or wounds of each patient being treated.

In one embodiment of the invention designed for multiple wounds in one area, the outer perimeter of the LED array 102' employs four 400–700 nanometer lasers 308a–d placed 90 degrees apart and each having an output power of less than about 1 milliWatt. Other targeting laser wavelengths and powers may be employed. Targeting lasers are widely available and may be obtained, for example, from Edmund Scientific.

The two vertical lasers (0 and 180 degree lasers—lasers 308b and 308d in FIG. 3A) may be "ranging" lasers adjusted so that their output beams intersect on a target area, such as the tissue target area 114', when the LED array 102' is positioned a predetermined distance from the target area (e.g., at 300 mm). The two horizontal lasers (90 and 270 degree lasers—lasers 308a and 308c in FIG. 3A) may be "positioning" lasers adjusted to produce two beams on the target area which are separated by a predetermined distance (e.g., 150 mm, 200 mm, 300 mm, etc.) when the ranging lasers 308b, 308d intersect (e.g., when the LED array 102' is the predetermined distance from the target area). Other numbers of ranging and positioning lasers may be employed, as may other laser wavelengths, spacings, intersection distances and positioning distances.

In another embodiment designed for large single wounds, a single laser that projects cross-hair 90 degree intersecting beams may be employed to provide simultaneous "ranging" and "positioning" beams that operate in essentially the same manner as the four laser embodiment described previously. For example, a single crosshair laser may be adjusted to produce crosshairs of a predetermined length (e.g., 150 mm, 200 mm, 300 mm, etc.) on the target area when the laser is positioned at a predetermined distance from the target area (e.g., 300 mm). When such a laser is employed, the target area may be delineated, for example, by an indelible marker with cross hairs spaced at the predetermined length (e.g., 150 mm) so that the crosshairs of the laser align with the target area delineations when the laser is positioned the predetermined distance from the target area (e.g., 300 mm). Other targeting techniques may be employed for ensuring accurate placement of the LED array.

As best shown in FIG. 3A, in at least one embodiment of the invention, the camera 110' is a charge coupled device (CCD) based digital camera that is located in an interior opening 310 of the LED array 102'. For example, the camera 110' may be a Quick-Cam Pro 3000 available from Logitech or another similar camera. The camera 110' may be pre-focused to permit retargeting and digital photo documentation of the same tissue/wound site. Further within this embodiment, one or more software programs stored within the computer 106' and the camera 110' may form a digital photo system that permits wound areas to be compared and represented as a percentage or square centimeter change in wound area to document healing. A slide show sequencing of overlay photographs over time may be employed to demonstrate stages of healing. Software also may be employed to permit a sequence of photographs to be "morphed" together into a continuous motion.

The LED array 102' and target positioning system 304 may be mounted on an articulating arm 108' that permits the LED array 102' to be positioned over a target area (e.g., 300 mm or another relevant distance over a patient's wound site in the above example) without physical contact. The programmable power source 104' and/or the computer 106' may be connected to the arm 108' and LED array 102' by one or more cables 312. Wireless connectivity also may be employed. In at least one embodiment, a 12-volt battery or a 120/240 VAC power supply powers the entire system.

Once the light therapy device 100' has been accurately placed over a target area such as the tissue target area 114', the target area (e.g., tissue/wound) may be photographed and the computer 106' may direct the programmable power source 104' to provide a specific series or combination of wavelengths/frequencies and intensities/durations (e.g., dosages) of LED light to the target area.

In at least one embodiment of the Invention, the LED array 102' is placed about 300 mm above the target area (e.g., a wound area to be exposed); and the lasers beams 307a, 307b (shown in the plane of FIG. 3B for reference purposes) from the ranging lasers 308b, 308d are placed to intersect at the proximal center 316 of the wound area. The positioning lasers 308a, 308c are adjusted horizontally so that their output beams 309a, 309b "straddle" the wound area on normal tissue that has been "marked" (e.g., with an indelible marker used to mark skin in plastic surgery) as shown by crosses 314a–b. Repeatable tissue dosing, dimensioning and photography thereby is ensured.

The target positioning system 304 thus allows repeatable placement of the LED array 102' relative to a target area such as a chronic wound or targeted tissues to facilitate repeatable LED dosages, photographs, wound measurements and text narrative to document clinical progress. A repeatable clinical dosing system for delivering a number of frequencies, intensities, and a repeatable duration of exposure thereby is provided.

With use of the embodiments of the present invention, sequencing of each of the four (or more) wavelengths in relation to each other is permitted. The invention also provides for complete repeatable dosage control for each exposure as well as a complete dosage record for each patient.

The foregoing description discloses only exemplary embodiments of the invention. Modifications of the above disclosed apparatus and method which fall within the scope of the invention will be readily apparent to those of ordinary skill in the art. For instance, instead of employing LEDs as light sources, lasers or other light sources may be employed. Other wavelengths than those described may be employed. For example, in one embodiment, the following wavelengths may be employed: 625 nm, 660 nm, 735 nm and 880 nm.

Indicator lights (not shown) may be mounted on the back of the LED array 102' to indicate which LED circuit/subarray has been activated.

In an least one embodiment, a CCD-type color camera may be employed as the camera 110'. The camera may be mounted inside the LED array 102', and a single cross hair laser may be positioned underneath the camera and tilted to intersect the crosshairs at the center of a TV camera field. Split screen software then may be employed on the computer 106' to allow a user to position a previously recorded image next to a realtime image. When the position of both images match, the realtime image may be recorded. Overlaying the images allows a user to observe wound healing.

Figure 4A:
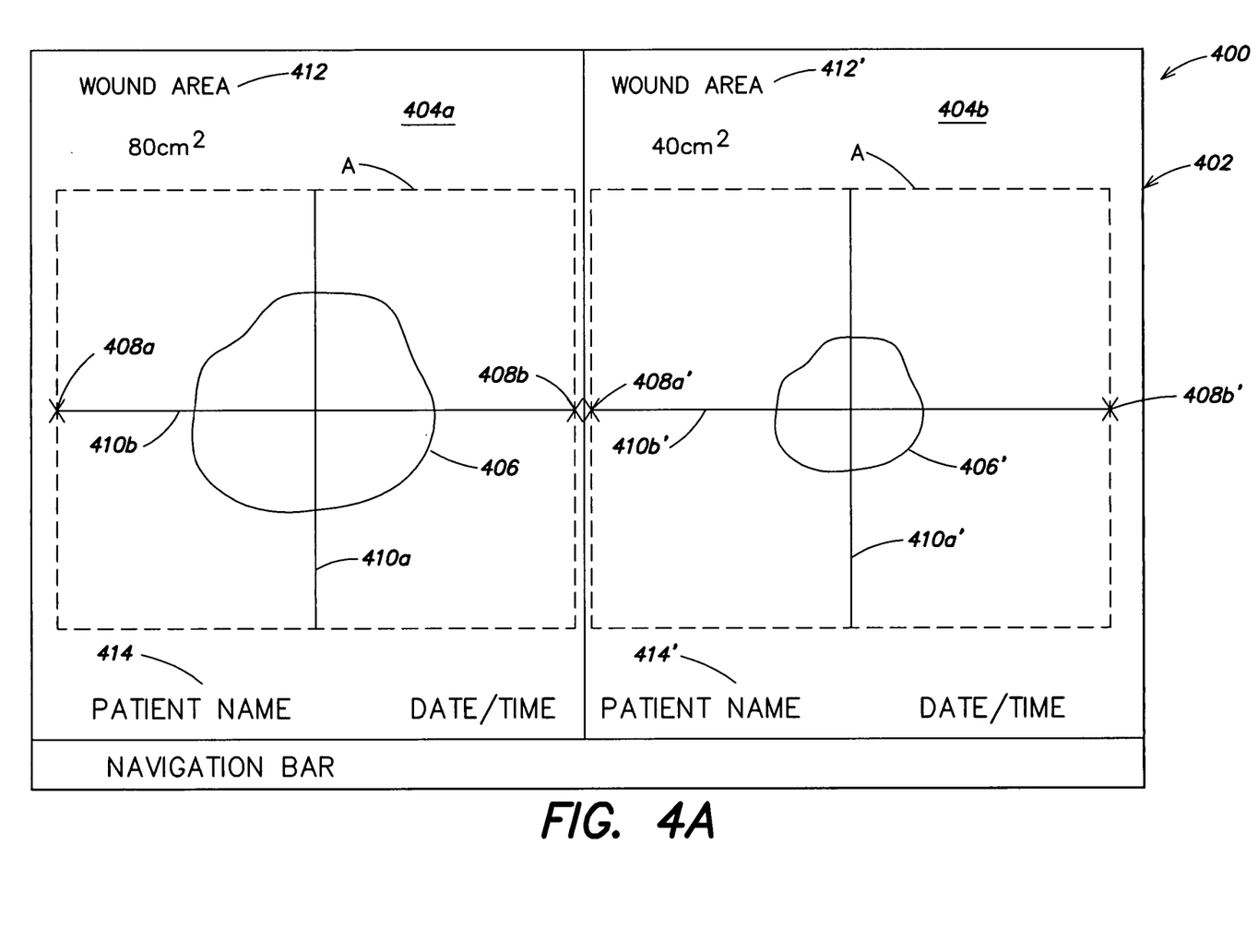
FIG. 4A illustrates an exemplary split screen interface provided in accordance with the present invention.

FIG. 4A illustrates an exemplary split screen interface 400 provided in accordance with the present invention. The split screen interface 400 may be displayed, for example, on a screen of the user device 106 (e.g., a laptop or other computer such as the computer 106'); and may be implemented via one or more computer program products stored, for example, in the user device 106.

With reference to FIG. 4A, the split screen interface 400 employs a window 402 having a first viewing area 404a and a second viewing area 404b. The first viewing area 404a is adapted to display a previously recorded image (e.g., an "historical" image) of a target area A (e.g., as captured by the camera 110) and the second viewing area 404b is adapted to display a realtime image of the target area A (e.g., as captured by the camera 110). The positioning of the historical and realtime images may be reversed. For clarity, reference numerals of like items within the second viewing area 404b (the realtime image area) will be differentiated with a single apostrophe.

In the embodiment of FIG. 4A, the target area A includes a wound 406 (406') that has been delineated by indelible markings 408a, 408b (408a', 408b'). Note that the image of the crosshairs of a targeting laser (e.g., a single crosshair laser) are also recorded by the camera 110 as indicated by reference numerals 410a, 410b (410a', 410b'). In at least one embodiment, the crosshairs 410a, 410b (410a', 410b') have a predetermined length (e.g., 150 mm) when the LED array 102 is positioned a predetermined distance (e.g., 300 mm) above the target area. In the embodiment of FIG. 4A, the markings 408a, 408b (408a', 408b') are spaced 150 mm apart. In this manner, a repeatable distance may be maintained between the target area and the LED array 102 merely by ensuring that the crosshair 410b (410b') contacts both markings 408a, 408b (408a', 408b').

As shown in FIG. 4A, the split screen interface 400 allows for easy comparison of a previously recorded image of the target area A (viewing area 404a) with a realtime image of the target area A (viewing area 404b). Wound size thereby may be easily compared (e.g., to determine healing progress/rate). In at least one embodiment, proper positioning of the LED array 102 may be determined by contacting an end of the historical image crosshair 410b with an end of the realtime image crosshair 410b' (as shown). Software preferably allows for calculation of wound area within the viewing areas 404a, 404b (e.g., to further aid in tracking healing). Various information such as wound area size 412

(412'), patient information 414 (414') or the like may be displayed within one or more of the viewing areas 404a, 404b.

Figure 4B:
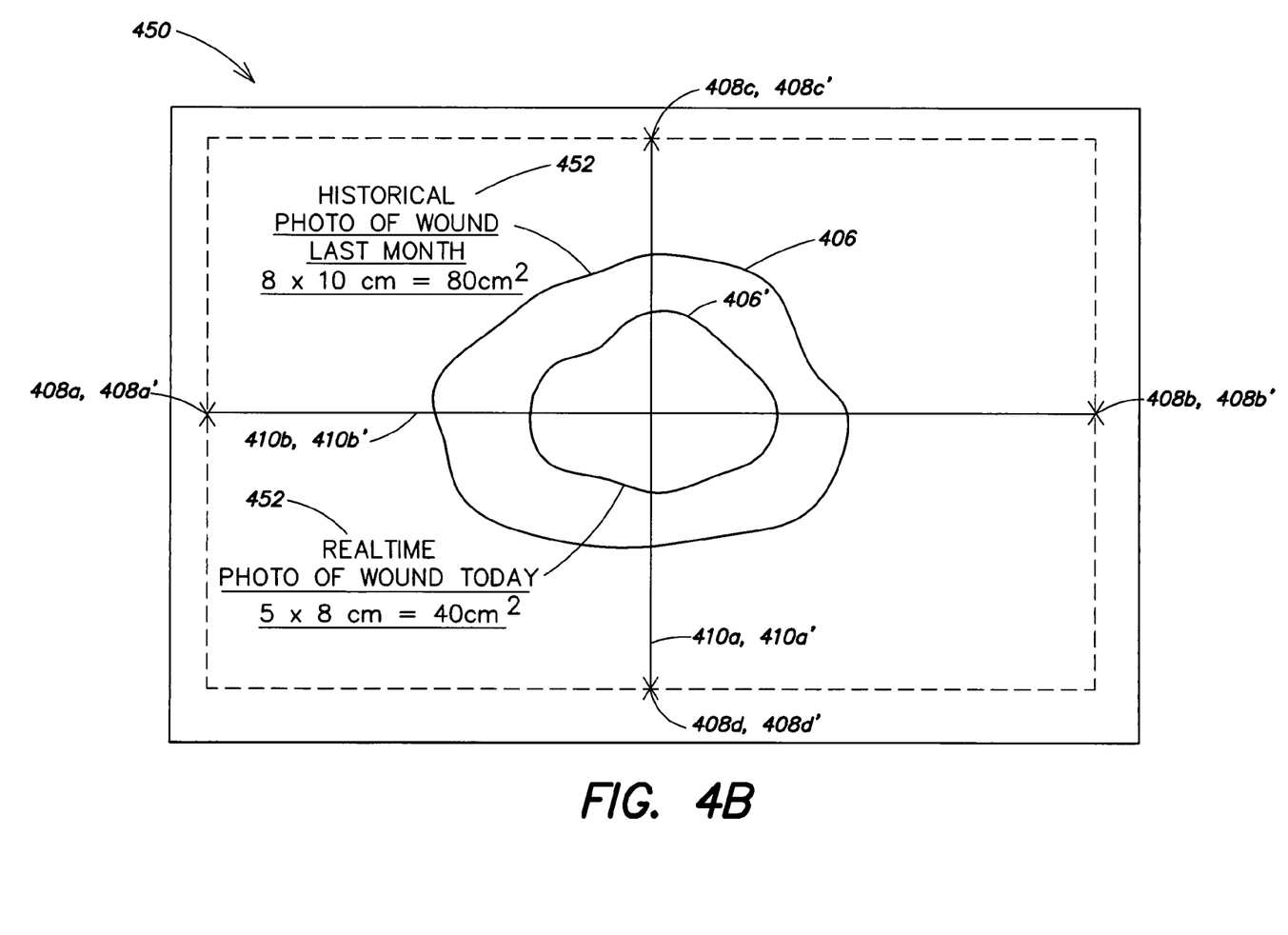
FIG. 4B illustrates an exemplary overlay screen interface provided in accordance with the present invention.

FIG. 4B illustrates an exemplary overlay screen interface 450 provided in accordance with the present invention. The overlay screen interface 450 may be displayed, for example, on a screen of the user device 106 (e.g., a laptop or other computer such as the computer 106'); and may be implemented via one or more computer program products stored, for example, in the user device 106.

The overlay screen interface 450 is similar to the split screen interface 400, but overlays the realtime image on the historical image as shown. Differences in wound area thereby are more readily observable, and positioning is simplified as proper positioning/alignment may be assured merely by overlaying historical image crosshairs 410a, 410b over realtime image crosshairs 410a', 410b'. Other user interfaces may be employed. Patient information (not shown), wound area information 452, etc., also may be displayed by the overlay screen interface 450.

As an example, a real-time image of a smaller wound (5×8 cm=40 cm$^2$) can be superimposed over a larger historical wound image so that both can be seen for comparison by moving the real-time LASER crosshair to cover the crosshair image from the historical image. This aligns the real-time image directly over the historical image for comparison. Any number of images may be "layered" on top of each other in a slideshow format, and slowly or rapidly sequenced from the oldest to the latest image. Software may be employed to compare and calculate a square centimeter (or other unit) area comparison between the historical and real-time images. This may be accomplished, for example, by "marking" the perimeter of the wound. The software then may compare the number of darker pixels inside the wound perimeter to the number of lighter pixels outside the wound perimeter. All images may be time/date stamped and saved as a retrievable file. In at least one embodiment, an image of a target area may not be saved without a patient number for identification.

The above described patient photo documentation system may also permit the historical and real-time images to be placed side by side for comparison (as shown in FIG. 4A). The historical image is placed on one side of a screen and the real-time image is placed on the other side of the screen. The real time image may be aligned using a LASER crosshair by connecting a horizontal LASER line of each image end to end.

Though the present invention has been described primarily with reference to non-contact applications (e.g., for sterility purposes), it will be understood that the LED array 102 (or 102') may be placed in contact with a target area. For example, the LED array may be implemented as a flexible (e.g., rubber pad) array, placed in a disposable container (e.g., a plastic bag) and placed directly on a wound site.

Figure 5A:
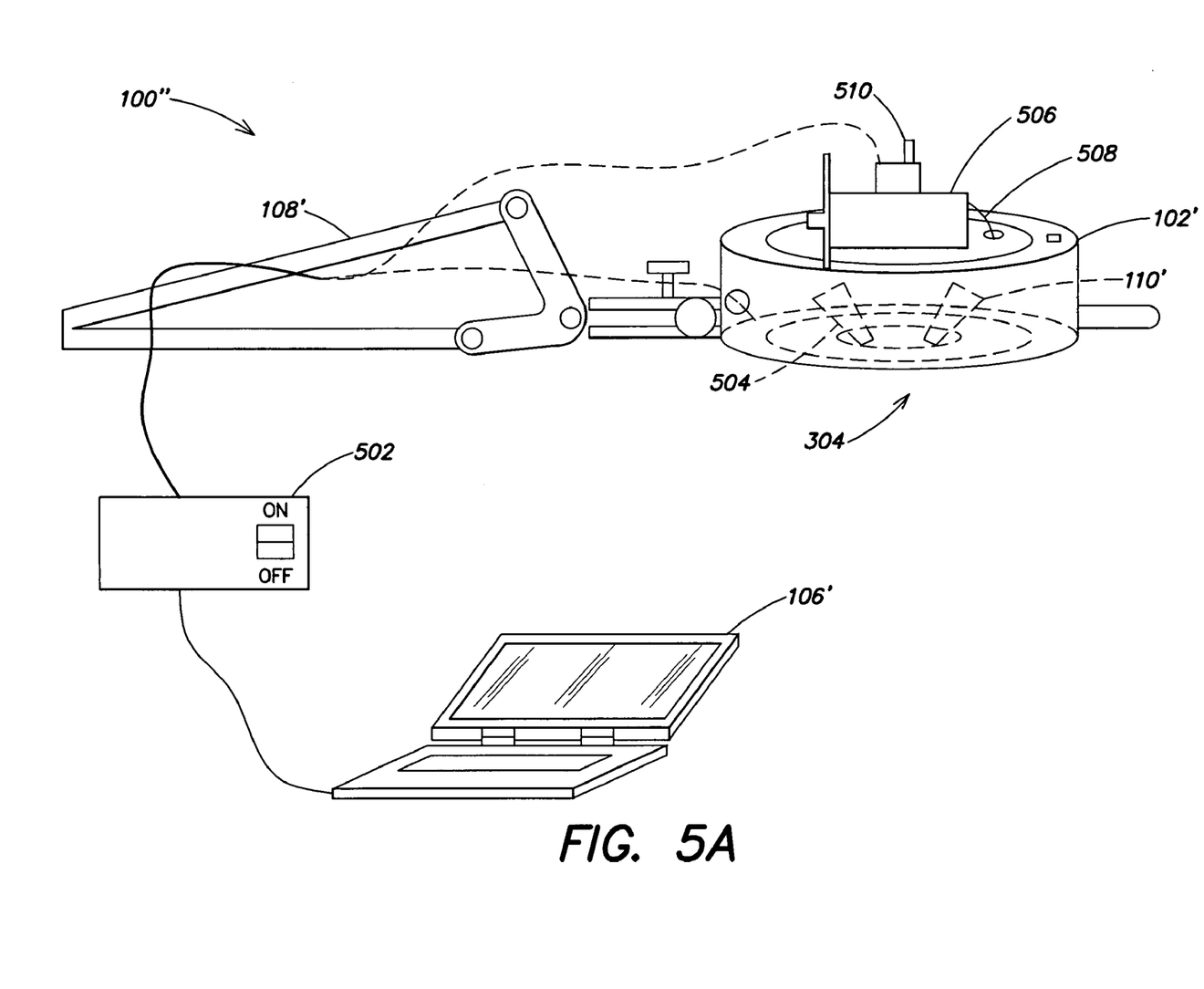
FIG. 5A is schematic side perspective view of an alternative embodiment of the light therapy device of FIGS. 3A and 3B.

FIG. 5A is schematic side perspective view of an alternative embodiment of the light therapy device 100' of FIGS. 3A and 3B (referred to by reference numeral 100" in FIG. 5A). The light therapy device 100" of FIG. 5A may be similar to the light therapy device 100' of FIGS. 3A–3B and include, for example, the LED array 102', a programmable controller and/or power source similar to programmable controller 104' of FIGS. 3A–3B (represented as interface 502 in FIG. 5A) and a user device such as the computer 106' (shown as a laptop computer in FIG. 5A, although any other computer may be employed). The computer 106', for example, may control operation of the light therapy device 100" (e.g., as previously described with reference to the light therapy device 100' of FIGS. 3A–3B).

The light therapy device 100" of FIG. 5A includes the target positioning system 304 of the light therapy device 100' of FIGS. 3A and 3B, which in the embodiment shown in FIG. 5A, includes a single targeting laser 504 (e.g., a single, crosshair laser), the camera 110' and in some embodiments a computer based text/photo documentation system (e.g., one or more software programs operable with the laptop or other computer 106'). The articulating arm 108' or another position adjustment mechanism also may be employed (as previously described).

The light therapy device 100" may include a power source 506 (that may be coupled to the LED array 102') for supplying power to the targeting laser 504 (e.g., via a power cord 508). An external power source also may be used. Preferably a switch 510 is provided that allows the targeting laser 504 to be turned on during positioning of the LED array 102' and turned off after positioning of the LED array 102', prior to employing the camera 110' to record an image of a target area. Other configurations may be employed. For example, the computer 106' may be used to automatically turn off the targeting laser 504 prior to image recording (e.g., instead of employing the switch 510). In some cases, it may be desirable to leave the targeting laser 504 on during image recording.

Figure 5B:
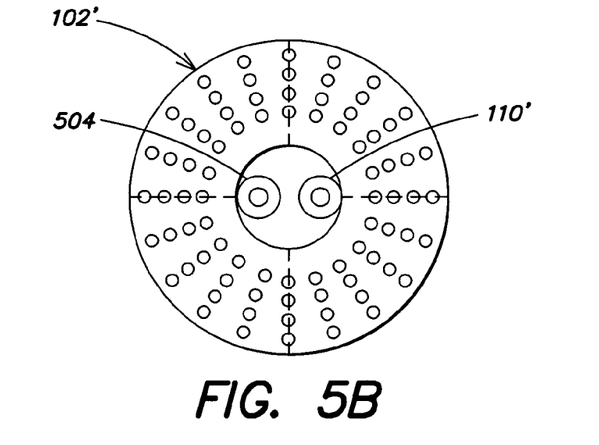
FIG. 5B is a schematic bottom view of the light array of FIG. 5A.
Figure 5C:
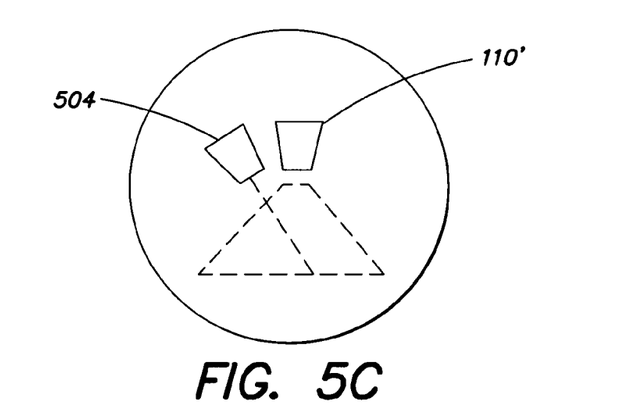
FIG. 5C is an enlarged view of the targeting laser and the camera of FIG. 5A.
Figure 5D:
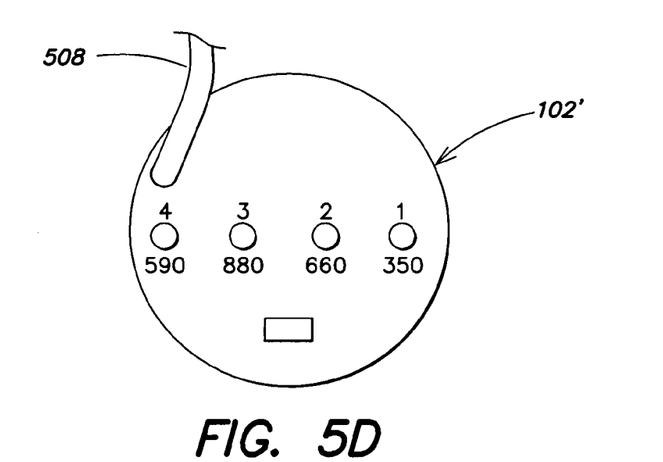
FIG. 5D is a schematic top view of the LED array of FIG. 5A.
Figure 5E:
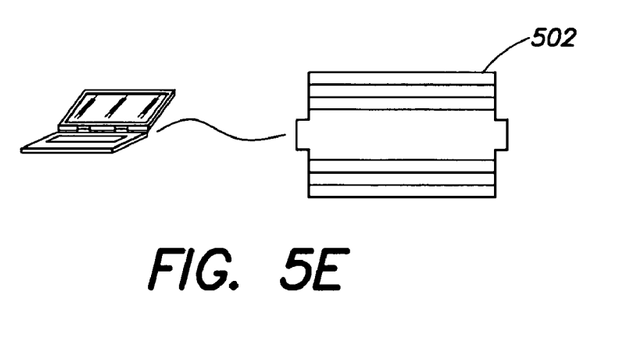
FIGS. 5E–G are schematic side, front and back views, respectively, of an exemplary embodiment of the interface of FIG. 5A.
Figure 5F:
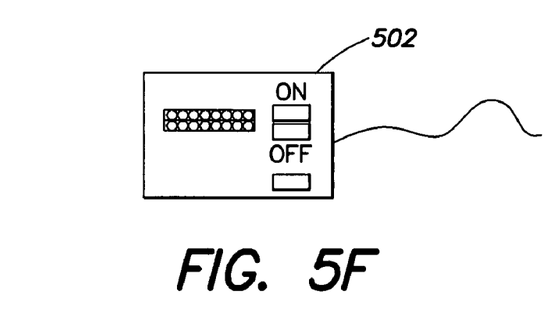
Figure 5G:
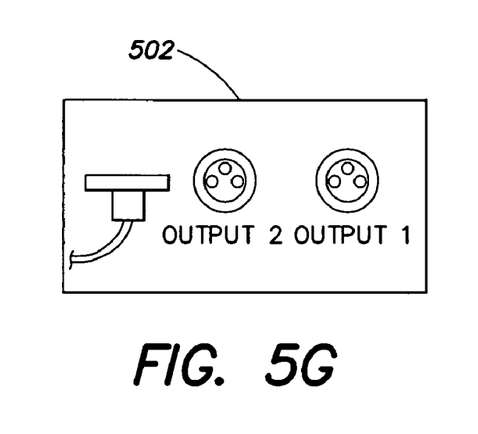

Further views of portions of the light therapy device 100" are shown in FIG. 5B which is a schematic bottom view of the light array 102' of FIG. 5A; FIG. 5C which is an enlarged view of the targeting laser 504 and the camera 110' of FIG. 5A; FIG. 5D which is a schematic top view of the LED array 102' of FIG. 5A; and FIGS. 5E–G which are schematic side, front and back views, respectively, of an exemplary embodiment of the interface 502.

Figure 5H:
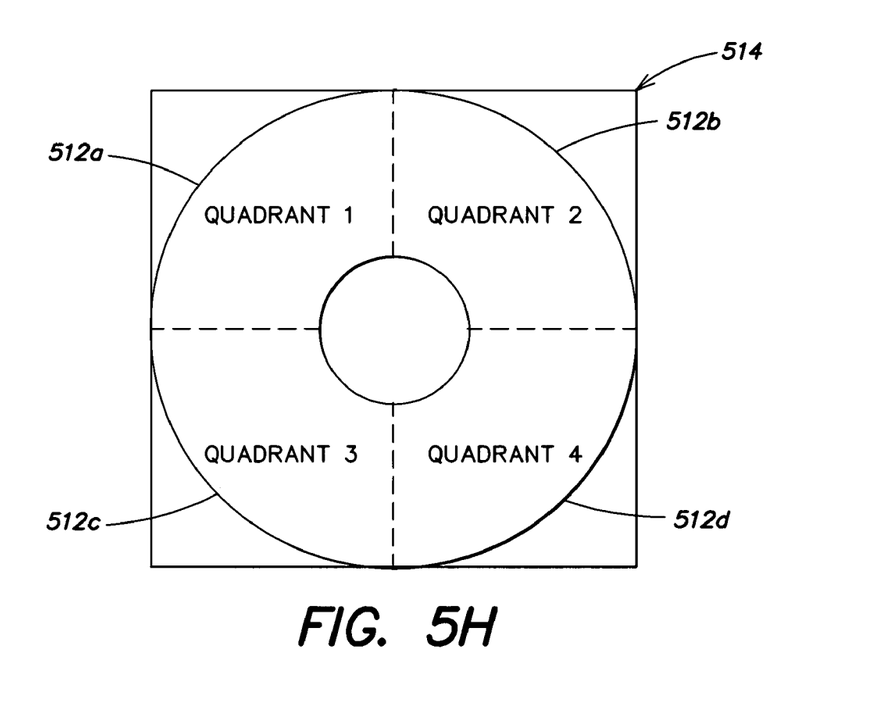
FIGS. 5H and 5I are a top schematic view and a side schematic view, respectively, of an embodiment of the LED array of FIG. 5A.
Figure 5I:
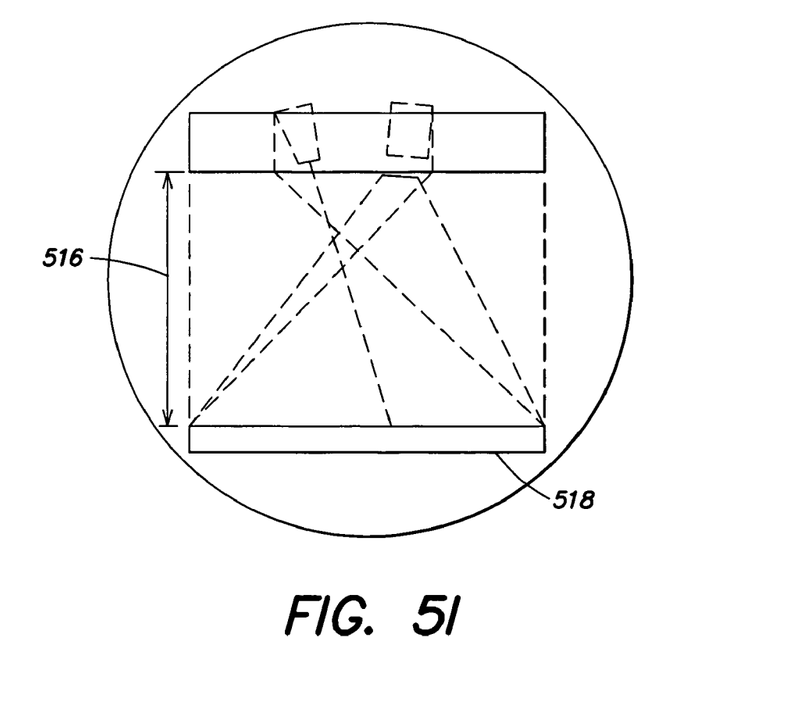

FIGS. 5H and 5I are a top schematic view and a side schematic view, respectively, of an embodiment of the LED array 102' of FIG. 5A wherein the LED array 102' is divided into four LED sub-arrays 512a–d. In at least one embodiment, each subarray is adapted to output a unique wavelength (e.g., 350, 590, 660 and 880 nanometers, although other frequencies may be employed). Other numbers of LED sub-arrays and other LED arrangements may be used. For example, LED's that output the same wavelength of light need not be grouped together (as previously described with reference to the LED array 102' of FIGS. 3A and 3B).

In at least one embodiment of the invention, each LED sub-array 512a–d is configured to output and focus light over a predefined area 514 when the LED array 102' is positioned at a predefined height 516 above a target area 518 (FIG. 5I). In the exemplary embodiment shown in FIGS. 5H–I, the predefined area 514 is about 150 mm when the LED array 102' is positioned at a predefined height 516 of 300 mm above the target area 518. Other predefined areas and/or heights may be employed. Note that the light beam of the targeting laser 504, the focus of the camera 110' and the focus of the LED sub-arrays 512a–d may be configured so as to intersect on the target area 518 within the predefined area 514 when the LED array 102' is positioned at the predefined height 516 (as shown in FIG. 5I). That is, when the LED array 102' is positioned at the predefined height 516, (1) the LED sub-arrays 512a–d may be configured to produce focused light beams on the target area 518 within the predefined area 514; (2) the targeting laser 504 may be configured to produce a crosshair or other identifying feature that fills, crosses or otherwise aligns with the target area 518 (such as described previously with reference to FIGS.

3A–4B); and (3) the camera 110' may be configured to provide a focused image of the predefined area 514.

In an alternative embodiment of the invention, rather than using the computer 106' or the switch 510 to turn off the targeting laser 504, the targeting laser 504 and/or the camera 110' may be controlled by an electronic sequencer such as a multi-position switch (not shown) positioned on the LED array 102' or at another suitable location. For example, in one embodiment, when the multi-position switch is not depressed, both the targeting laser 504 and the camera 110' are off (or in a standby mode). When the multi-position switch is slightly depressed, the targeting laser 504 is turned on, allowing the LED array 102' to be accurately positioned relative to a target area (as previously described). When the multi-position switch is fully depressed, the targeting laser 504 is turned off, and the camera 110' is directed to record an image of the target area. Alternatively, or additionally, full depression of the multi-position switch may initiate a predetermined dose of light to be delivered to the target area via the LED array 102'.

In one embodiment of the invention, the electronic sequencer, the targeting laser 504, the camera 110' and/or the LED array 102' may work in cooperation with the computer 106'. For example, depression of the electronic sequencer may signal the computer 106' to (1) turn on or off the targeting laser 504; (2) record an image with the camera 110'; and/or (3) direct the LED array 102' to deliver a predetermined light dose to a target. Likewise, dedicated control logic (not shown) may allow/direct the electronic sequencer, the targeting laser 504, the camera 110' and/or the LED array 102' to so operate. Note that any of the above described embodiments for the light therapy device 100" may operate in a manner similar to the light therapy device 100' of FIGS. 3A and 3B, and may be employed with a split and/or overlay screen interface in a manner similar to that described with reference to FIGS. 4A and 4B.

In general, repeatable measurements and documentation (e.g., imaging) of wounds during wound treatment is difficult, whether or not light therapy is employed. For instance, wounds typically are documented weekly and often by different people using different photography techniques.

The inventive target positioning systems described above may be employed to document any wound treatment (e.g., whether or not light therapy is employed). Such systems may permit exact positioning of a camera relative to a wound (e.g., using one or more lasers coupled to the camera that ensure that the camera is precisely positioned/focused relative to a target).

Figure 6:
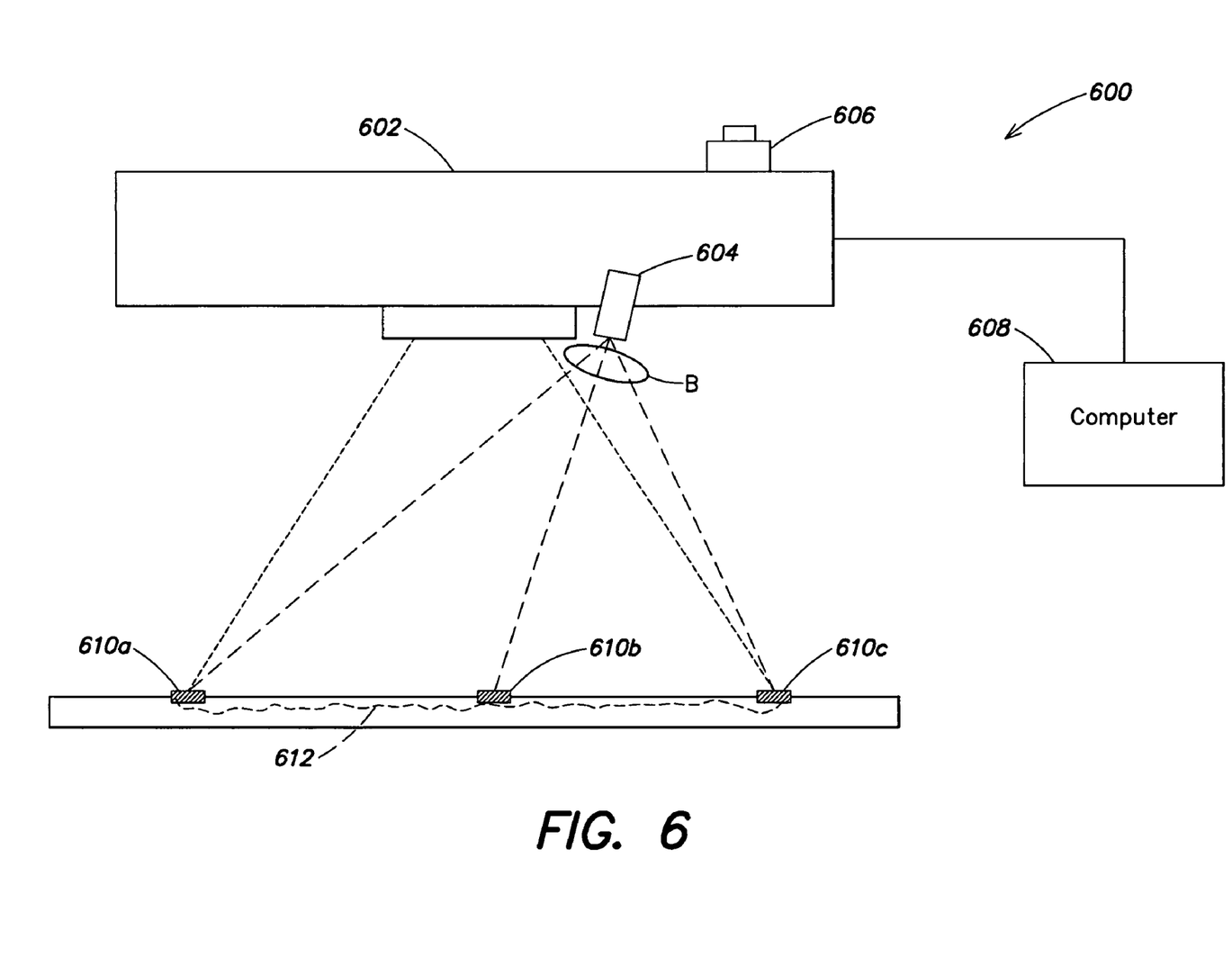
FIG. 6 is a schematic diagram of an exemplary embodiment of an inventive wound documentation system provided in accordance with the present invention.

FIG. 6 is schematic diagram of an exemplary embodiment of an inventive wound documentation system 600 provided in accordance with the present invention. The wound documentation system 600 comprises a digital (or other suitable) camera 602, and at least one targeting laser 604 and an electronic sequencer 606 (e.g., a multi-position switch) coupled to the camera 602. The camera 602 may or may not be coupled to a computer or other controller 608 (e.g., an appropriately programmed laptop or desktop computer, personal digital assistant, hand held video game player such as a GameBoy™, etc.).

In one embodiment of the invention, the targeting laser 604 comprises a crosshair laser that is affixed to the camera 602 and aligned to focus at a center of the optical field of the camera 602. (Another type of laser, an LED or some other light source also may be used.) Such a crosshair laser may produce a fan shaped, XY crosshair beam B on a target area, wherein each beam leg changes length as the camera 602/laser 604 are moved toward or away from the target area (as shown in FIG. 6). Other targeting lasers and/or alignment configurations may be employed.

The electronic sequencer 606 may comprise, for example, a multi-position switch. In at least one embodiment, the multi-position switch may be a momentary (e.g., multi-circuit N/O–N/C) three stage switch that allows the targeting laser 604 to be turned on to align the camera 602, but turned off prior to image capture by the camera 602 (thereby eliminating the laser beam B from any recorded image). For example, the multi-position switch may have:

(1) a static (e.g., spring biased) position in which the targeting laser 604 is off (or in standby) and the camera 602 is off (or in standby);

(2) a first detent position in which the targeting laser 604 is on and the camera 602 is off (or in standby); and (3) a second (e.g., fully depressed) detent position in which the targeting laser 604 is off and the camera 602 records an image.

Other configurations may be employed.

In operation, two or more marks or other indicators 610a–c (three of which are shown in FIG. 6) are made on a perimeter of a wound area 612 (e.g., using an indelible dermal marker pencil or other marking device). The two or more marks 610a–c preferably are placed peri-wound at a known distance (e.g., 200 mm in one embodiment, although other distances may be employed).

Thereafter, the electronic sequencer 606 is depressed to its first detent position to turn on the targeting laser 604, and the camera 602, and the targeting laser 604 coupled thereto, are moved toward or away from the marks 610a–c until the crosshairs of the laser beam B align exactly between the marks 610a–c. Once the crosshairs of the laser beam B of the targeting laser 604 are aligned with the marks 610a–c, the electronic sequencer 606 may be depressed (e.g., further) to the second detent position so as to turn off the targeting laser 604 and record an image with the camera 602.

The camera 602, the targeting laser 604 and/or the entire wound documentation system 600 may be self contained and may, for example, employ a diskette, memory chip or other storage medium for image storage. In the embodiment shown in FIG. 6, the camera 602 is coupled to the computer 608 which may be equipped with a larger memory system and digital imaging software in order to add patient information (e.g., name) to a photo/image, print pictures for inclusion in a medical chart or the like. The system 600 also may scale wound X-Y dimensions and area using the known distance between the markings 610a–c. The wound documentation system 600 may employ a split and/or overlay screen interface in a manner similar to that described with reference to FIGS. 4A and 4B (e.g., to allow side-by-side or overlap time lapsed sequencing of wound treatment/healing images).

Fewer or more marks 610a–c than described may be used (e.g., one or two, more than three, etc.). An articulating arm or other positioning mechanism may be employed with the wound documentation system 600 to assist in positioning of the camera 602. (Likewise, an articulating arm need not be employed with any of the light therapy devices described herein).

Accordingly, while the present invention has been disclosed in connection with exemplary embodiments thereof, it should be understood that other embodiments may fall within the spirit and scope of the invention, as defined by the following claims.

The invention claimed is:

1. An apparatus for use in light therapy comprising:
   at least one light emitting diode array adapted to emit a wavelength of light;
   a targeting mechanism coupled to the at least one light emitting diode array so as to allow light emitted from the at least one light emitting diode array to be repeatably positioned on a target area during non-contact light therapy;
   an imaging mechanism adapted to record an image of a target area,
   wherein the targeting mechanism is coupled to the imaging mechanism and includes at least one targeting light source, the at least one targeting light source adapted to allow the imaging mechanism to be repeatably positioned on a target area prior to image recording during each of a plurality of different non-contact light therapy treatments so as to provide clinically repeatable dosages sufficient to have a therapeutic effect, and
   wherein the apparatus further comprises a sequencer mechanism having:
   a first position in which the at least one targeting light source is off and the imaging mechanism does not record an image;
   a second position in which the targeting light source is on and the imaging mechanism does not record an image; and
   a third position in which the targeting light source is off and the imaging mechanism records an image.

2. The apparatus of claim 1 wherein the at least one light emitting diode array comprises a plurality of light emitting diode arrays, each light emitting diode array adapted to emit a different wavelength of light.

3. The apparatus of claim 2 wherein each light emitting diode array includes a plurality of light emitting diodes and wherein light emitting diodes that emit different wavelengths are uniformly interdispersed.

4. The apparatus of claim 3 wherein each light emitting diode is adapted to emit a wavelength of 625 nm, 660 nm, 735 nm or 880 nm.

5. The apparatus of claim 3 wherein each light emitting diode is adapted to emit a wavelength of 350, 590, 660 or 880 nanometers.

6. The apparatus of claim 1 further comprising a positioning device coupled to the at least one light emitting diode array and adapted to position the at least one light emitting diode array relative to a target area.

7. An apparatus for use in light therapy comprising:
   at least one light emitting diode array adapted to emit a wavelength of light;
   a targeting mechanism coupled to the at least one light emitting diode array so as to allow light emitted from the at least one light emitting diode array to be repeatably positioned on a target area during non-contact light therapy;
   an imaging mechanism adapted to record an image of a target area; and
   a sequencer mechanism having:
   a first position in which the at least one targeting light source is off and the imaging mechanism does not record an image;
   a second position in which the targeting light source is on and the imaging mechanism does not record an image; and
   a third position in which the targeting light source is off and the imaging mechanism records an image,
   wherein the targeting mechanism is coupled to the imaging mechanism and includes at least one targeting light source, the at least one targeting light source adapted to allow the imaging mechanism to be repeatably positioned relative to the target area prior to image recording.

8. A method comprising:
   storing a first image of a treatment area at a time T1;
   displaying a second image of the treatment area at a time T2;
   positioning a light emitting diode array to provide a light therapy treatment to the treatment area at the time T2 based upon a comparison of the first and second images.

9. The method of claim 8 wherein the positioning is further based upon information from a ranging mechanism.

10. The method of claim 8 wherein positioning the light emitting diode array is performed based on superimposing the second image on the first image.

* * * * *